(12) United States Patent
Kretzschmar et al.

(10) Patent No.: US 8,658,808 B2
(45) Date of Patent: Feb. 25, 2014

(54) PROCESS FOR THE PRODUCTION OF DRONEDARONE INTERMEDIATES

(75) Inventors: Gerhard Kretzschmar, Frankfurt am Main (DE); Volker Kraft, Frankfurt am Main (DE); Kai Rossen, Frankfurt am Main (DE); Joachim Graeser, Frankfurt am Main (DE)

(73) Assignee: Sanofi, Paris (FR)

( * ) Notice: Subject to any disclaimer, the term of this patent is extended or adjusted under 35 U.S.C. 154(b) by 178 days.

(21) Appl. No.: 13/322,094

(22) PCT Filed: May 26, 2010

(86) PCT No.: PCT/EP2010/057272
§ 371 (c)(1),
(2), (4) Date: Nov. 22, 2011

(87) PCT Pub. No.: WO2010/136502
PCT Pub. Date: Dec. 2, 2010

(65) Prior Publication Data
US 2012/0077995 A1    Mar. 29, 2012

Related U.S. Application Data

(60) Provisional application No. 61/244,547, filed on Sep. 22, 2009.

(30) Foreign Application Priority Data

May 27, 2009 (EP) .................................... 09290394

(51) Int. Cl.
*C07D 307/80* (2006.01)

(52) U.S. Cl.
USPC ........................................................ 549/467

(58) Field of Classification Search
USPC ........................................................ 549/467
See application file for complete search history.

(56) References Cited

U.S. PATENT DOCUMENTS

| 3,577,441 A | 5/1971 | Kaminsky et al. |
| 3,657,350 A | 4/1972 | Mooradian et al. |
| 5,223,510 A | 6/1993 | Gubin et al. |
| 2012/0065411 A1 | 3/2012 | Kretzschmar et al. |

FOREIGN PATENT DOCUMENTS

| EP | 0471609 A1 | 2/1992 |
| FR | 2 809 397 A1 | 11/2001 |
| FR | 2 833 259 A1 | 6/2003 |
| WO | WO 01/28974 A2 | 4/2001 |
| WO | WO 01/29019 A1 | 4/2001 |
| WO | WO 02/48078 A1 | 6/2002 |
| WO | WO 03/040120 A1 | 5/2003 |
| WO | WO 2006/021304 A1 | 3/2006 |
| WO | WO2007/140989 A2 | 12/2007 |
| WO | WO2009/044143 A2 | 4/2009 |
| WO | WO 2010/136500 A1 | 12/2010 |

OTHER PUBLICATIONS

International Preliminary Report on Patentability dated Nov. 29, 2011 issued in PCT/EP2010/057272.
Weitkamp, et al., Isomorphe Substitution in Zeolithen: Katalyse an Boro-, Alumo-und Gallo-Silicaten mit ZSM-5-Struktur, Chem.-Ing.-Tech., vol. 58, (1986), No. 12, pp. 969-971.
Adams, et al., Quinone Imides. XXXIX. Adducts of Quinone Monoimides and Conversion of Active Methylene Adducts to Benzofurans, Journal of the American Chemical Society, vol. 78, No. 3, (1956), pp. 658-663.
Delahay, et al., Past and Recent Approaches of Preparing Fe-ZSM-5. Current Topics in Catalysis, (2007), vol. 6, pp. 19-33.
Fieser, et al., Reagents for Organic Synthesis, John Wiley & Sons, p. 703-705 (1967).
Horton, et al., [65] Reactions With Reactive Alkyl Halides, J. Methods in Enzymology, vol. 11, pp. 556-565, (1967).
Imori, et al., Efficient Demethylation of N,N-Dimethylanilines With Phenyl Chloroformate in Ionic Liquids, Synlett. (2006), No. 16, pp. 2629-2632.
Laszlo, et al., 65 Catalysis of Friedel-Crafts Alkylation by a Montmorillonite doped with Transition-Metal Cations, Helvetica Chimica Acta, vol. 70, (1987), pp. 577-586.
Majdik, Studiul Reactiei de Ciclizare a Orto-Hidroxibenzilfenilcetonelor in Benzofuran Derivati, Revista De Chimie, vol. 36, No. 8, pp. 760-761, (1985).
Majdik, et al., O-Arilcetoxime I. O-Arilarea Cetoximelor cu Nitroclorbenzeni, Revista De Chimie, vol. 40, No. 6, (1989), pp. 490-493.
Majdik, et al., O-Arilcetoxime II. Prepararea Unor 2-(Aril)-Nitrobenzofurani Din O-(Nitrofenil)-Acetofenonoxime, Revista De Chimie, vol. 40, No. 8, (1989), pp. 689-693.

(Continued)

*Primary Examiner* — Taofiq A Solola
(74) *Attorney, Agent, or Firm* — Scully, Scott, Murphy & Presser, P.C.

(57) ABSTRACT

A process for the production of Dronedarone intermediates of the formula (I), by acylation of 2-(2-hydroxy-5-nitrophenyl)-1-(4-methoxyphenyl)-ethanone, subsequent treatment of the ester with bases and a zeolite (alumosilicate) catalyst and optional subsequent demethylation. This process can be used for the production of Dronedarone.

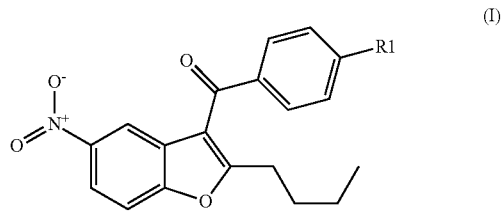

(I)

12 Claims, No Drawings

(56) References Cited

OTHER PUBLICATIONS

Nagy, et al., Isomorphous Substitution in Zeolites, Mol. Sieves, (2007), vol. 5, pp. 365-478.
Nakamura, et al., Pyrazole Derivatives as New Potent and Selective 20-Hydroxy-5,8,11,14-Eicosatetraenoic Acid Synthase Inhibitors, Bioorganic & Medicinal Chemistry, vol. 12, (2004), pp. 6209-6219.
Skeels, et al., Zeolite Chemistry, Substitution of Iron or Titanium for Aluminum in Zeolites via Reaction With the Respective Ammonium Fluoride Salts, ACS Symposium Series, Zeolite Synthesis, (1989), vol. 398, pp. 420-435.
Fontana, et al., Syntheses of (R,S)-Naproxen and its 6-O-Desmethylated Metabolite Labelled With 2H. Journal of Labelled Compounds and Radiopharmaceuticals, (2008), vol. 51, pp. 239-241.
Majdik et al., "Prepararea unor 2-(aril)-nitrobenzofurani din O-(nitrofenil)-acetofenonoxime," Revista de Chemie, vol. 40, No. 8, pp. 689-693.
Majdik et al., "O-Arilarea cetoximelor cu nitroclorbenzeni," Revista de Chemie (1989), vol. 40, No. 6, pp. 490-493.
Castellino, Angelo J. et al., "Synthesis of Benzofurans from Oxygenated Phenoxyamines," Journal of Organic Chemistry (1984), vol. 49, pp. 4399-4404.
Delahay, Gerard et al., "Past and recent approaches of preparing Fe-ZSM-5," Current Topics in Catalysis (2007), vol. 6, pp. 19-33.
Skeels, Gary W. et al., "Substitution of Iron or Titanium for Aluminum in Zeolites via Reaction with the Respective Ammonium Fluoride Salts," American Chemical Society (1989), pp. 420-435.
Laszlo, Pierre et al., "Catalysis of Friedel-Crafts Alkylation by a Montmorillonite Doped with Transition-Metal Cations," Helvetica Chimica Acta (1987), vol. 70, pp. 577-586.
Nagy, J.B. et al., "Isomorphous Substitution in Zeolites," Mol Sieves (2007), vol. 5, pp. 365-478.

Weitkamp, Jens et al., "Isomorphe Substitution in Zeolithen: Katalyse an Boro-, Alumo-und Gallo-Silicaten mit ZSM-5-Struktur," Chem-Ing-Tech (1986), vol. 58, No. 12, pp. 969-971.
Gutowski, Keith E. et al., "Prediction of the Formation and Stabilities of Energetic Salts and Ionic Liquids Based on ab Initio Electronic Structure Calculations," The Journal of Physical Chemistry B (2005), vol. 109, pp. 23196-23208.
Cheng, Lili et al., "Facile Cleavage of Ethers in Ionic Liquid," Bulletin of the Chemical Society of Japan (2007), vol. 80, No. 10, pp. 2008-2010.
Headley, Lindsay Sanders et al., "Dynamic Solvation in Imidazolium-Based Ionic Liquids on Short Time Scales," Journal of Physical Chemistry (2006), vol. 110, pp. 9549-9554.
Fieser et al., Reagents for Organic Synthesis, J. Wiley, NY (1967), vol. 1, pp. 703-705.
Pal, Santanu Kumar et al., "Synthesis of monohydroxy-functionalized triphenylene discotics: green chemistry approach," Tetrahedron (2007), vol. 63, pp. 6874-6878.
Boovanahalli, Shanthaveerappa K. et al., "Application of Ionic Liquid Halide Nucleophilicity for the Cleavage of Ethers: A Green Protocol for the Regeneration of Phenols from Ethers," Journal of Organic Chemistry (2004), vol. 69, pp. 3340-3344.
Chauhan, Shive M.S. et al., "Microwave assisted dealkylation of alkyl aryl ethers in ionic liquids," Journal of Chemical Research (2004), p. 693-694.
Liu, Tao et al., "Cleavage of Methyl Ethers of Flavones by Chloroaluminate Ionic Liquid," Synthetic Communications (2004), vol. 34, pp. 3209-3218.
Weissman, Steven A. et al., "Recent advances in ether dealkylation," Tetrahedron (2005), vol. 61, pp. 7833-7863.
Wu, Ha-Hong et al., "Immobilization of HX: [HMIM]X as Halogenating Agent, Recyclable Catalyst and Medium for Conversion of Alcohols to Alkyl Halides," Chinese Journal of Chemistry (2004), vol. 22, pp. 619-621.
International Search Report dated Aug. 26, 2010 issued in PCT/EP2010/057272.

PROCESS FOR THE PRODUCTION OF DRONEDARONE INTERMEDIATES

CROSS-REFERENCE TO RELATED APPLICATIONS

This application claims the benefit of U.S. Provisional Application No. 61/244,547 filed on Sep. 22, 2009.

A process for the production of Dronedarone intermediates of the formula I

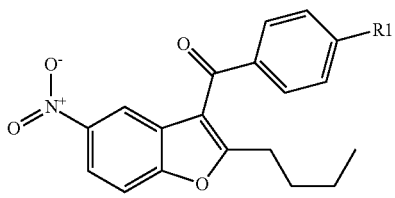

by acylation of 2-(2-hydroxy-5-nitrophenyl)-1-(4-methoxyphenyl)-ethanone, subsequent treatment of the ester with bases and a zeolite (alumosilicate) catalyst and optional subsequent demethylation. This process can be used for the production of Dronedarone.

The present invention relates to a chemical process for the manufacture of 2-n-butyl-3-(4-methoxybenzoyl)-5-nitrobenzofuran of the formula I, wherein R1 is OMe, (=compound of the formula Ia) and 2-n-butyl-3-(4-hydroxybenzoyl)-5-nitrobenzofuran of the formula I, wherein R1 is OH; (=compound of the formula Ib) which are both key intermediates for the production of N-(2-n-butyl-3-{4-[3-(dibutylamino)-propoxy]-benzoyl}-benzofuran-5-yl)methanesulfonamide of the formula II (Dronedarone).

Dronedarone is a drug for the treatment of arrhythmia (U.S. Pat. No. 5,223,510) and several prior art methods are disclosed for its preparation. These methods involve stepwise procedures via a number of intermediates, of which two examples are 2-n-butyl-5-nitrobenzofuran of the formula III and 2-n-butyl-3-(4-methoxybenzoyl)-5-nitrobenzofuran of the formula Ia.

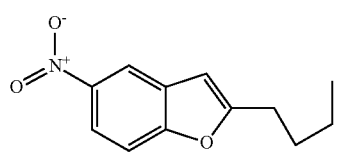

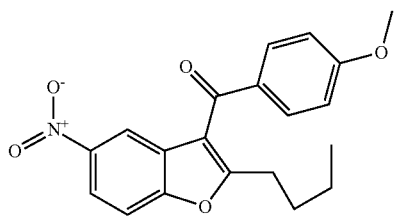

The intermediate of the formula III is prepared by multistage processes from 4-nitrophenol as described in U.S. Pat. No. 5,223,510 and H. R. Horton and D. E. Koshland, J. Methods in Enzymology, Vol. 11, 556, (1967) or from salicylaldehyde as described in WO0128974 and WO0129019.

The intermediate of the formula Ia is conventionally prepared from the intermediate of the formula III by Friedel Crafts benzoylation with anisoyl chloride and heavy metal Lewis-acids, like tin-tetrachloride or iron(III)chloride as catalysts in halogenated or non-halogenated solvents, as described in WO2007140989 and other references described therein. The intermediate of the formula Ib is conventionally prepared from the intermediate of the formula Ia by demethylation.

It is an object of the present invention to provide a novel process for the preparation of the Dronedarone intermediates of the formula I starting from commercially available materials and from compounds described already in the literature, themselves being prepared easily from commercially available materials, by using simple and environmentally compatible reagents and solvents, to afford high overall yields and good purity of the products.

The above object is achieved in accordance with the present invention by preparing an intermediate of the formula I leading to Dronedarone starting with commercially available compounds such as 4-methoxyacetophenone, 4-chloronitrophenol and valeric acid chloride (pentanoylchloride).

One aspect of the present invention thus relates to a process for preparing a compound of the formula I,

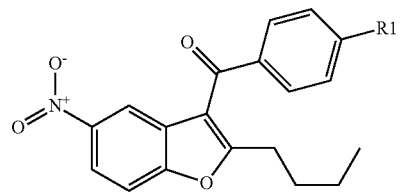

wherein
R1 is methoxy or hydroxyl;
and salts thereof;
which comprises, as shown in scheme 1, ridine, NaOH, KOH, $Na_2CO_3$ and $K_2CO_3$. In one embodiment base A is preferably $Na_2CO_3$ and $K_2CO_3$.

In a special embodiment step 1 comprises at first as shown in scheme 2 the neutralisation of the acidic OH-moiety in the Scheme 1

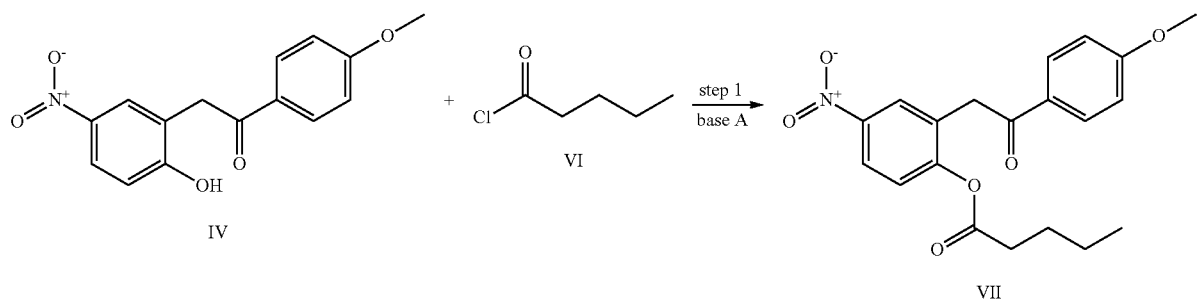

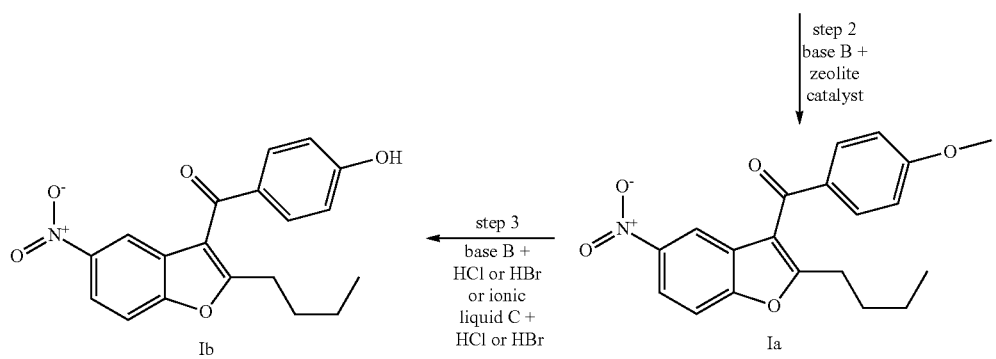

a) acylation of the 2-(2-hydroxy-5-nitrophenyl)-1-(4-methoxyphenyl)-ethanone of the formula IV by the acid chloride of formula VI in the presence of a base A providing the new ester of the formula VII (step 1);
b) heating of the ester of the formula VII with a base B and a zeolite (alumosilicate) catalyst providing the benzofuran of the formula Ia (step 2);
c) optionally heating of the benzofuran of formula Ia with HCl or HBr in the presence of the base B or alternatively heating of the benzofuran of formula Ia with HCl or HBr in an ionic liquid C providing the compound of the formula Ib (step 3).

The preparation of the starting material of the formula IV is explicitly described in the literature (for example U.S. Pat. No. 3,657,350, U.S. Pat. No. 3,577,441, C. Majdik et al., Revistade Chimie 40 (6), 490-3 (1989) and 40 (8), 689-93 (1989) (Bukarest)). The acid chloride of the formula VI is commercially available.

The following describes each of the distinct process steps of the invention in more detail:

Step 1 describes the esterification of the compound of the formula IV with the acid chloride of the formula VI which requires base A to neutralize the acid which is liberated in the esterification step. At least one equivalent of such base is needed for this purpose, its nature being not critical, since any base neutralizing HCl can be taken, including a metal carbonate, a metal hydroxide, a metal alcoholate, a tertiary amine, or the like. Examples of base A are triethylamine, diisopropylethylamine, tri-n-butylamine, pyridine, 4-dimethylaminopycompound of the formula IV with one of the above-mentioned hydroxides or carbonates (base A*) in order to obtain the crystalline sodium or potassium salt of the formula V, Scheme 2

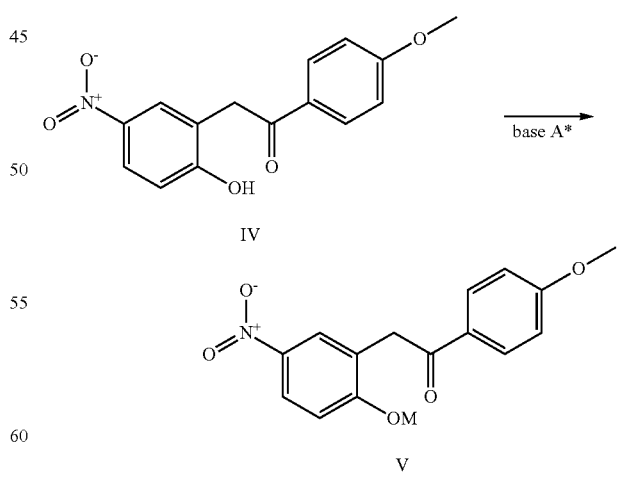

wherein M is Na or K and wherein base A* is a metal carbonate or a metal hydroxide, for example NaOH, KOH, $Na_2CO_3$ and $K_2CO_3$, preferably $Na_2CO_3$ and $K_2CO_3$.

The sodium or potassium salts of formula V can be used as a stable storage form.

For instance, the phenol of the formula IV can be dispersed in a minimum amount of water and neutralized with approximately one base equivalent of above base A* at 0° C. to 100° C., preferably at 0° C. to 50° C. The resulting sodium or potassium salt of the formula V, respectively, can be isolated, for example by precipitation, and can be filtered and dried afterwards. Alternatively, the salts of the formula V can be prepared in organic solvents, for example acetone, methylethylketone or acetonitrile, preferably acetone, by neutralisation with about one equivalent of said bases in water at 0° C. to 100° C., preferably at 0° C. to 50° C., for example at 40-50° C., and the products can be isolated, for example by evaporation of the solvents.

In one embodiment of the invention the phenol ester of the formula VII can be obtained by mixing the phenol of the formula IV with one equivalent amount or a slight excess, for example 1.0 to 1.5 equivalents, of the acid chloride of the formula VI in an inert organic solvent, for example N,N-dimethylformamide, tetrahydrofuran, acetone, dichloromethane, methyl-isobutyl ketone, acetonitrile, 2-methyl-tetrahydrofuran, 1,4-dioxan, toluene, benzene, ethyl acetate or isopropyl acetate, with base A, at −20° C. to +50° C., preferably at 0° C.-20° C. The product of the formula VII can be isolated in a way known by a person skilled in the art. For example by washing away excess acid and acid chloride with diluted aqueous bases, for example $NaHCO_3$ or $KHCO_3$, washing away excess base with diluted aqueous acids, for example HCl, citric acid or $NaH_2PO_4$, preferably HCl, drying the organic phase for example with $MgSO_4$ or $Na_2SO_4$, and evaporation of solvents.

Alternatively, the respective sodium or potassium salt of the formula V can be combined with about one equivalent of the acid chloride of the formula VI in a volatile inert organic solvent for example tetrahydrofuran, acetone, dichloromethane, methyl-ethyl ketone, methyl-isobutyl ketone, acetonitrile, 2-methyl-tetrahydrofuran, 1,4-dioxan, toluene, preferably acetone, at −20° C. to +50° C., preferably at −10° C. to 20° C. The reaction solution can be directly subjected to the subsequent step 2 or the product can be isolated by filtration from the precipitated sodium or potassium chloride and evaporation of solvents.

By any procedure described here, the ester of the formula VII is obtained in practically quantitative yield and good purity for the following reaction step 2.

Step 2 comprises the heating of the ester of the formula VII with a base (base B) and a zeolite (alumosilicate) catalyst in a solvent to give the benzofuran of formula Ia. For that purpose, the ester of the formula VII is dissolved or suspended in an inert organic solvent containing the dispersed zeolite, preferably in a minimum amount of an inert organic solvent, for instance in N,N-dimethylformamide, tetrahydrofuran, methyl-isobutyl ketone, methyl-ethyl ketone, acetonitrile, 2-methyl-tetrahydrofuran, 1,4-dioxan, toluene, benzene, ethyl acetate, butyl acetate, isopropyl acetate, N-methyl-pyrrolidone, chlorobenzene or xylene, preferably in xylene or toluene, with one equivalent or a slight excess, for example 1.0 to 2.0 equivalents, of base B.

Examples for base B performing the desired process include tertiary amines like diisopropylethylamine, tri-n-butylamine, tri-n-propylamine, N,N-dimethyaniline, N,N-diethylaniline, N-methyl-imidazole, N-ethyl-imidazole, N-propyl-imidazole, N-butyl-imidazole, collidine, 2,6-lutidine, 1,4-diazabicyclo-[2,2,2]-octane, 2,2,6,6-tetramethylpiperidine and quinuclidine. The preferred base B is selected from the group of diisopropylethylamine, tri-n-butylamine, tri-n-propylamine, N,N-dimethyaniline, N,N-diethylaniline, N-methyl-imidazole, N-ethyl-imidazole, N-propyl-imidazole, N-butyl-imidazole.

The zeolite catalyst in step 2 can be an unmodified (natural or synthetic) or modified zeolite catalyst or a mixture of said catalysts.

Examples for zeolite catalysts performing the desired process include natural and synthetic alumosilicates of the formula $M^1xM^2yM^3z[(Al_2O_3)_{12}(SiO_2)_{12}]$ which are commercially available or can be prepared by a person skilled in the art by known procedures and wherein $M^1$, $M^2$ and $M^3$ are metals and x/y/z denote the composition of the respective metal cations required to compensate for the 12 negative charges of the alumino-silicate framework. As described in L. F. Fieser & M. Fieser, Reagents for Organic Synthesis, John Wiley & Sons, page 703-705 (1967), typical metal cations M include potassium, sodium, calcium and magnesium in widely variable compositions, and certain commercially available zeolites have homogeneous metal cation and variable water content, for instance the molecular sieves of the formula $Na_{12}[(Al_2O_3)_{12}(SiO_2)_{12}]$ with 0.4 nm pore size which are commercially available from Sigma-Aldrich and other suppliers. Examples for natural zeolites performing the process include bentonite and montmorillonite which have similar molecular compositions and ion exchange properties.

Further types of zeolite catalysts performing the desired process include alumosilicates which are prepared by partial exchange of at least one of the metal cations contained in the zeolites of the formula $M^1xM^2yM^3z[(Al_2O_3)_{12}(SiO_2)_{12}]$ by any other metal cations M, preferably with variable amounts of iron, manganese, titanium, zirconium, zinc or scandium. These modified zeolites provide higher catalytic activity in performing the desired process at lower reaction temperatures and in shorter reaction times to achieve complete conversion.

Modified zeolites can be purchased from commercial sources or they are prepared by persons skilled in the art according to literature procedures, for example by simple ion exchange in liquid phase, by solid-solid-exchange, sublimation methods or by hydrothermal synthesis as described in Review about Fe-zeolites like Fe-ZSM-5: G. Delahay et al., Current Topics in Catalysis (2007), 6, 19-33; Publisher: Research Trends;

Review about Fe, Ti-zeolites: G. W. Skeels, E. M. Flanigan, ACS Symposium Series (1989), 398 (Zeolite Synth.), 420-435;

Review about Fe, Ti, Mn, Zn-zeolites: J. B. Nagy et al., Molecular Sieves (2007), 5 (Characterization II), 365-478 and other articles in this book, Publisher: Springer GmbH, Berlin, Heidelberg);

Article about Fe, Ti, Zr-zeolites: J. Weitkamp et al., Chem.-Ing.-Technik 58 (1986), 12, 969-971 and references therein.

Preparation Fe-, Ti-, Zr-, Zn-doped montmorillonite catalysts: P. Lazlo, A. Mathy, Helv. Chim. Acta, vol. 70, 577-586 (1987)

These modified or unmodified zeolites are conveniently applied as powders, pellets or sticks and have variable water content and pore size depending on their preparation procedures. Typical pore sizes range from 0.3 nm to 15 nm.

The temperature for the reaction in process step 2 can be from 50° C. to 250° C., preferably from 60° C. to 140° C.

The reaction rates of step 2 are variable and, as a person skilled knows, depend on the base, the zeolite catalyst, the solvent and the temperature selected for this process. A typical reaction time when using tri-n-butylamine as a base, xylene as solvent and a commercially available unmodified zeolite (e.g. a molecular sieve of 0.5 nm pore size) ranges from 8 to 16 hours when the reaction temperature ranges from 140° C. to 100° C. A typical reaction time when using the same base (tri-n-butylamine) and a commercial molecular sieve which has been modified by exchange with $Fe^{3+}$ ions ranges from one hour to 15 minutes when the reaction temperature ranges from 110° C. (reflux temperature in toluene) to 140° C. (reflux temperature in xylene). High turnover rates in this reaction step and highly pure products are achieved when anhydrous reagents, notably solvents, bases and zeolites are used and when the water is removed by azeotropic distillation during the reaction course.

The benzofuran of the formula Ia can be isolated, for example by filtration of the reaction solution from the mineral and evaporation of the solvent and the base. If isolated in this way or prepared by any other means, the compound of the formula Ia may be subjected to the next step 3 comprising the demethylation reaction into the phenol of formula Ib.

Step 3 comprises the heating of the benzofuran of the formula Ia with base B and HBr or HCl in a solvent or without a solvent or alternatively heating of the benzofuran of formula Ia with HCl or HBr in an ionic liquid C to give the demethylated benzofuran of formula Ib. The appropriate solvents and bases B are the same as defined for step 2 of the process.

The solvent and the base B used in step 3 of the process can independently of each other be identical or different to the solvent and base B used in step 2, preferably in step 3 the same solvent and base B is used as in step 2.

Examples of an ionic liquid C used in step 3 are compounds of formula VIII or IX

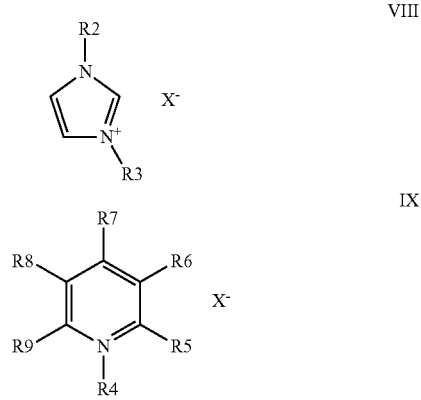

wherein R2, R3 and R4 are independently of each other alkyl having 1, 2, 3, 4, 5, 6 or 7 carbon atoms, R5, R6, R7, R8 and R9 are independently of each other H or alkyl having 1, 2, 3, 4, 5, 6 or 7 carbon atoms and X is F, Cl, Br, I, tetrafluoroborate, hexafluorophosphate, trifluoromethanesulfonate or hexafluoroantimonate, preferable X is F, Cl, Br, I or tetrafluoroborate. Preferably the ionic liquid C is selected from the group of 1-butyl-4-methylpyridinium tetrafluoroborate, 1-butyl-pyridinium chloride, 3-butyl-1-methyl-3H-imidazolium chloride, 3-ethyl-1-methyl-3H-imidazolium chloride, 1-butyl-2-methylpyridinium tetrafluoroborate, 1-butyl-3-methylpyridinium tetrafluoroborate, 1-butyl-pyridinium tetrafluoroborate, 3-butyl-1-methyl-3H-imidazolium tetrafluoroborate and 3-ethyl-1-methyl-3H-imidazolium tetrafluoroborate, for example selected from the group of 1-butyl-4-methylpyridinium tetrafluoroborate, 1-butyl-pyridinium chloride, 3-butyl-1-methyl-3H-imidazolium chloride and 3-ethyl-1-methyl-3H-imidazolium chloride.

The compounds of formula VIII or IX are commercially available or can be prepared according to, or in a similar manner to, processes which are described in the literature and familiar to those skilled in the art.

In one embodiment of the invention a mixture of the isolated benzofuran of formula Ia and 1.0 to 10 equivalents, preferably 1.3 to 3 equivalents, of the hydrochloride or hydrobromide salt of the respective base B is heated with or without a solvent at the appropriate temperature until complete conversion of the benzofuran of formula Ia into the phenol of formula Ib. The hydrochloride or hydrobromide salt of the base B is prepared by mixing HCl or HBr with the respective base B.

In another embodiment of the invention 1.0 to 10 equivalents, preferably 1.3 to 3 equivalents, of the base B and 1.0 to 10 equivalents, preferably 1.3 to 3 equivalents, of HCl or HBr are added to the isolated benzofuran of formula Ia and the mixture is heated with or without a solvent at the appropriate temperature until complete conversion of the benzofuran of formula Ia into the phenol of formula Ib.

In another embodiment of the invention the reaction mixture obtained from step 2 is separated from the zeolite catalyst by filtration or centrifugation, optionally the solvent is evaporated and subsequently the required amount of gaseous HCl or HBr (1.0 to 10 equivalents, preferably 1.3 to 3 equivalents) is added to the remaining mixture composed of the benzofuran of formula Ia and the base B from step 2 to provide in situ the hydrochloride or hydrobromide salt of the base B. Subsequently the mixture is heated at an appropriate temperature until complete conversion of the benzofuran of formula Ia into the phenol of formula Ib.

In the above described embodiments the appropriate temperature for the reaction in process step 3 can be from 120° C. to 250° C., preferably from 140° C. to 200° C. The reaction rates of step 3 are variable and, as a person skilled knows, depend on the hydrohalide salt of the base B and the temperature selected for this process. The typical reaction time when using tributylamine-hydrochloride ranges from one hour to 12 hours when the reaction temperature ranges from 200° C. to 140° C.

In another embodiment of the invention the isolated benzofuran of formula Ia is heated in an ionic liquid C and 1.0 to 10 equivalents, preferably 1.3 to 3 equivalents, of HCl or HBr are added and the mixture is heated at the appropriate temperature until complete conversion of the benzofuran of formula Ia into the phenol of formula Ib In this embodiment the appropriate temperature for the reaction in process step 3 can be from 130° C. to 170° C., preferably from 130° C. to 145° C. The reaction rates of step 3 are variable and, as a person skilled knows, depend on an ionic liquid C and the temperature selected for this process. The typical reaction time when using ionic liquids C ranges from 3 hours to 20 hours when the reaction temperature ranges from 130° C. to 170° C. The ionic liquid C can be regained and recycled.

The benzofurans of the formulas Ia and Ib can be isolated with methods known to those skilled in the art. These procedures can include an aqueous work-up of the reaction mixture or a chromatography of the reaction mixture. An example of an easy work-up procedure involves removing excessive base B, for example by distillation or by washing the mixture with an aqueous acid and then crystallizing the product from a solvent or from mixtures of solvents like methyl-tert.-butylether, heptane, diisopropylether, hexane or methanol. Alternatively, the desired product can be obtained by a chromatographic purification.

Another aspect of the invention is directed to a process for preparing a compound of the formula Ia

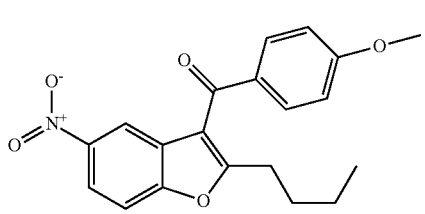

and salts thereof;
which comprises, as shown in scheme 3,

Scheme 3

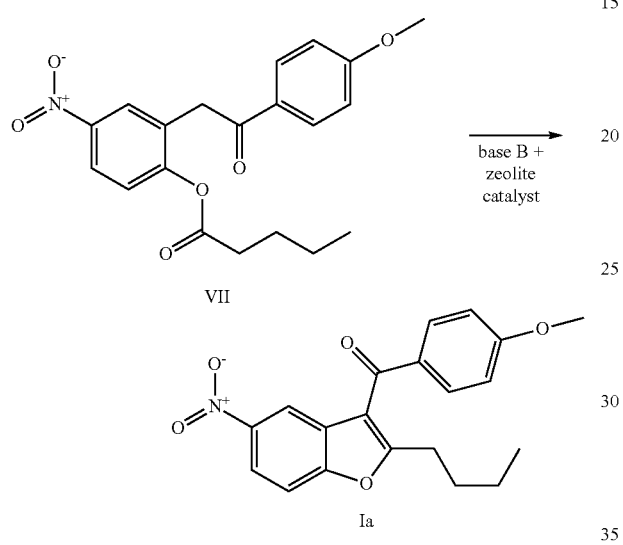

heating a compound of the formula VII with a base B and a zeolite catalyst.

This process corresponds to step 2 in scheme 1 described above and comprises, therefore, the same reaction conditions as described above.

Another aspect of the invention is directed to the process for preparing a compound of the formula Ib

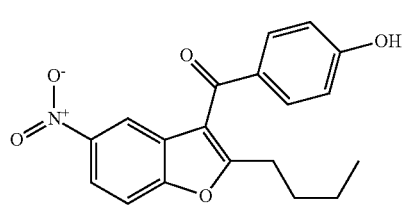

and salts thereof;
which comprises, as shown in scheme 4,

Scheme 4

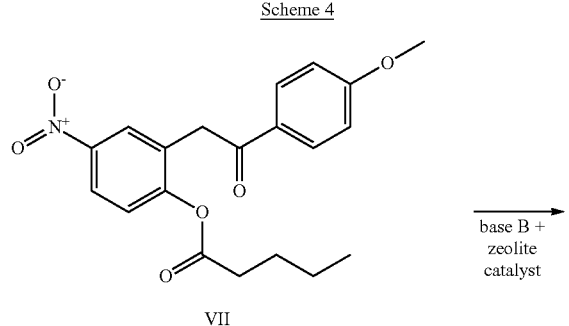

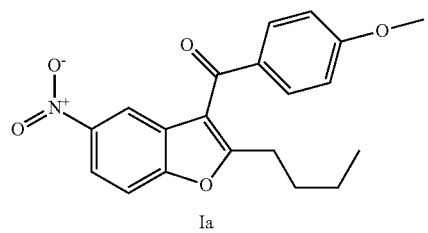

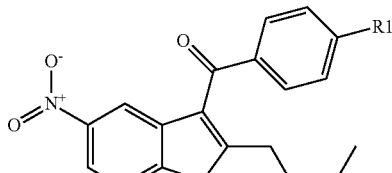

a) heating the ester of the formula VII with a base B and a zeolite (alumosilicate) catalyst providing the benzofuran of the formula Ia;

b) heating of the benzofuran of the formula Ia with HCl or HBr in the presence of the base B or alternatively heating of the benzofuran of formula Ia with HCl or HBr in an ionic liquid C providing the compound of the formula Ib.

This process corresponds to steps 2 and 3 in scheme 1 described above and comprises, therefore, the same reaction conditions as described above.

Another aspect of the present invention thus relates to a process for preparing a compound of the formula I, wherein
R1 is methoxy or hydroxyl;
and salts thereof;
which comprises, as shown in scheme 5, Scheme 5

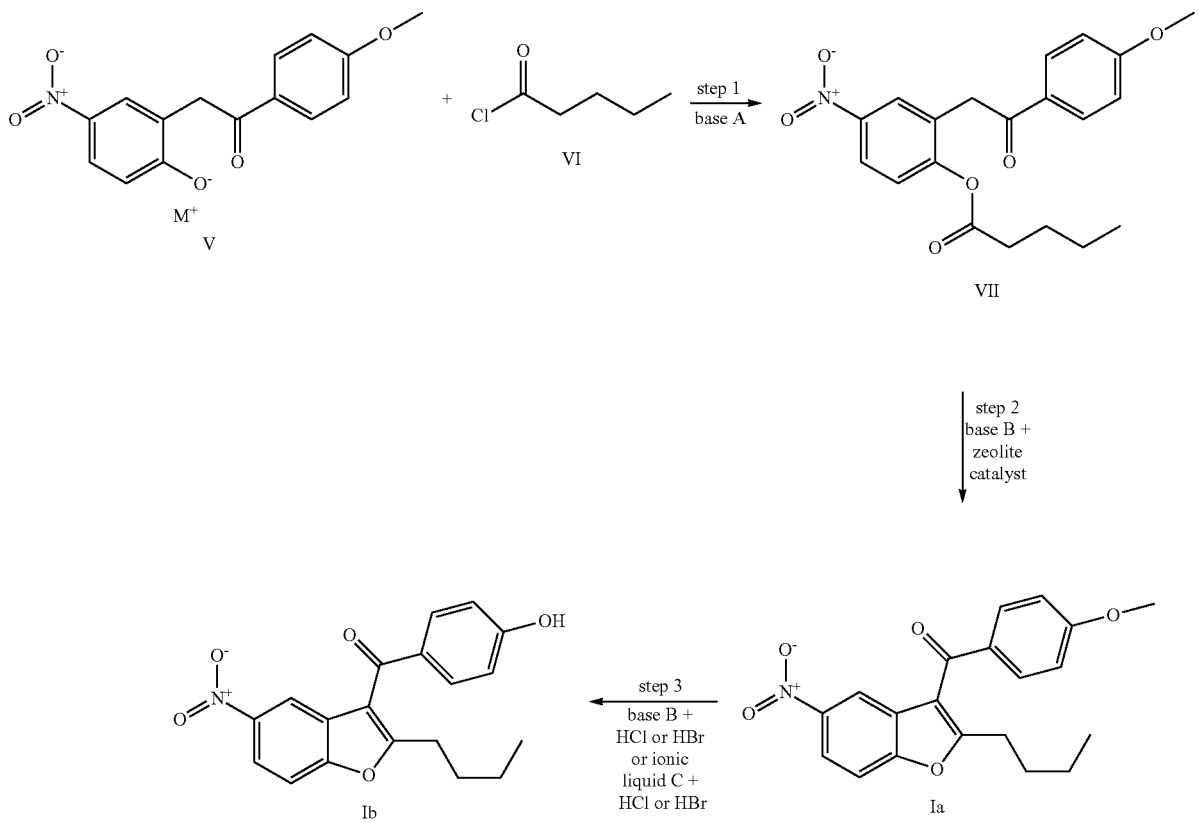

a) reacting a compound of the formula V, wherein M is Na or K, with an acid chloride of the formula VI in the presence of a base A providing the ester of the formula VII;
b) heating of the ester of the formula VII with a base B and a zeolite (alumosilicate) catalyst providing the benzofuran of the formula Ia;
c) optionally heating of the benzofuran of formula Ia with HCl or HBr in the presence of the base B or alternatively heating of the benzofuran of formula Ia with HCl or HBr in an ionic liquid C providing the compound of the formula Ib.

This process corresponds to steps 1, 2 and 3 in scheme 1 described above and comprises, therefore, the same reaction conditions as described above.

Another aspect of the present invention relates to a process for preparing a compound of the formula Ib,

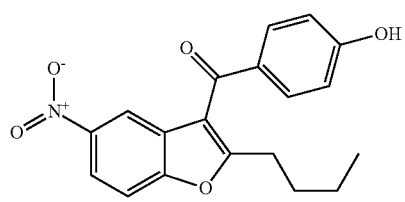

and salts thereof;
which comprises, as shown in scheme 6,

Scheme 6

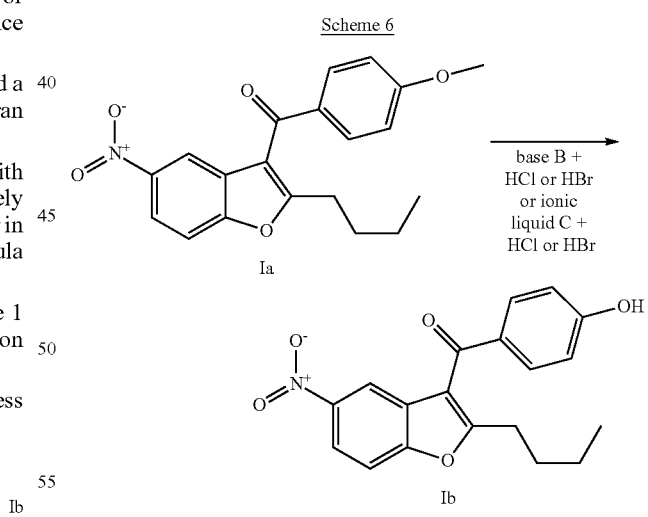

heating of the benzofuran of formula Ia with HCl or HBr in the presence of the base B or alternatively heating of the benzofuran of formula Ia with HCl or HBr in an ionic liquid C providing the compound of the formula Ib.

This process corresponds to step 3 in scheme 1 described above and comprises, therefore, the same reaction conditions as described above.

The compound of the formulae IV, V and VII may be present in the form of all their tautomeric forms, unless they are more precisely defined. For example the compounds of the formula V may also be present as tautomers (keto or enol form) or as a mixture of tautomeric structures:

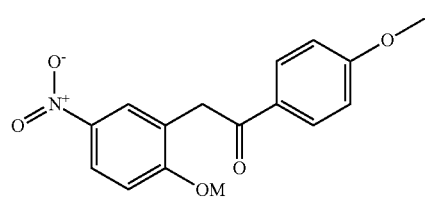 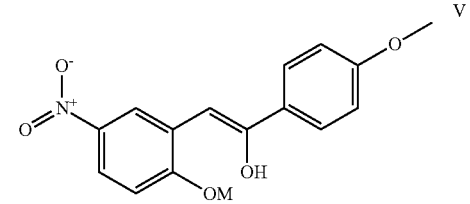

For the purpose of the present invention the compounds of the formulae I and IV to VII can be used in form of all derivatives, for example solvates such as hydrates and alcohol adducts, of the formulae I and IV to VII. The invention likewise encompasses all crystal modifications of the compounds of the formulae I and IV to VII.

The above-described compounds of the formulae I, IV and VI to VIII may be used in the process according to the invention in the form of their salts or in salt free form and/or may be isolated in the form of their salts or in salt free form. Salts may be obtained by the customary methods, for example by reacting with acids or bases in a solvent, or by anion exchange or cation exchange from other salts. Useful acid addition salts are, for example, halides, in particular hydrochlorides and hydrobromides, lactates, sulfates, citrates, tartrates, acetates, phosphates, methylsulfonates, benzenesulfonates, p-toluenesulfonates, adipates, fumarates, gluconates, glutamates, glycerolphosphates, maleates, benzoates, oxalates and pamoates and trifluoroacetates. If the compounds of the formulae I, IV, VI and VII contain an acid group, they are capable of forming salts with bases, for example as alkali metal salts, preferably sodium or potassium salts, or as ammonium salts, for example as salts with ammonia or organic amines or amino acids. They can also be present as zwitterions. In the case of the preparation of active ingredients, preference is given to physiologically tolerated salts and pharmaceutically acceptable salts.

ABBREVIATIONS ca. circa
h hour(s)
i.vac. in vacuum
LC-MS liquid chromatography-mass spectrometry
Me methyl
MIBK methyl-isobutyl ketone
MTBE methyl-tert.-butylether
NMR Nuclear magnetic resonance
HPLC High performance liquid chromatography
Rt Retention time
THF tetrahydrofuran

EXAMPLES

This invention is described in more detail by the examples that follow. These examples are designated to illustrate the invention, but do not limit its scope. Each step of the process described in the present invention may be operated either batch by batch or as a continuous process, or semicontinuous mode, and is scalable on larger amounts than described here.

The NMR assignments are for illustration only based on analysis of the one-dimensional $^1$H NMR spectra as done by those skilled in the art. A more detailed analysis of the spectra may lead to minor reassignments of some NMR peaks, which obviously does not change the overall assignment. All $^1$H NMR spectra are recorded on a 500 MHz instrument, shifts are relative to TMS in [ppm], the solvent is always DMSO-$d_6$.

Example 1

Synthesis of 2-(2-hydroxy-5-nitrophenyl)-1-(4-methoxyphenyl)-ethanone potassium salt (a compound of the formula V, M=K)

10.0 g (34.8 mmol) of 2-(2-hydroxy-5-nitrophenyl)-1-(4-methoxyphenyl)-ethanone (compound of the formula IV), prepared according to literature procedures (as described in U.S. Pat. No. 3,657,350, U.S. Pat. No. 3,577,441, C. Majdik et al., Revistade Chimie 40 (6), 490-3 (1989) and 40 (8), 689-93 (1989) (Bukarest)), were dissolved in 100 ml of acetone and stirred with a solution of 2.53 g (18.3 mmol) of potassium carbonate in 20 ml of distilled water for 1 h at 40-50° C. The solvents were evaporated and the remaining yellow solid was dried i. vac. to yield 11.3 g (99.8%) of the title compound.

LC-MS purity>98% (MN$^+$ 287).

The $^1$H NMR spectrum detected the presence of a mixture of keto- and enol-forms: 3.80, 3.78 (2s, OMe), 3.93 (s, CH$_2$ keto-form), 5.97 (d, =CH enol-form).

Example 2

Synthesis of 2-(2-pentanoyloxy-5-nitrophenyl)-1-(4-methoxyphenyl)-ethanone (compound of the formula VII)

4.23 g (35.0 mmol) of valeroyl chloride (compound of the formula VI) were added with cooling at −10° C. to 20° C. to a stirred suspension of 11.3 g (34.7 mmol) of 2-(2-hydroxy-5-nitrophenyl)-1-(4-methoxyphenyl)-ethanone potassium salt (example 1) in 50 ml of dry acetone. After 30 minutes the reaction was complete, as monitored by LC-MS, and the mixture was filtered through a layer of Celite to remove the precipitated potassium chloride. The solution was evaporated to dryness to give 9.23 g (98%) of a yellow oil which slowly crystallized while standing at room temperature.

$^1$H NMR (DMSO-$d_6$): 0.75 (t, 3H, CH$_3$), 1.20, 1.45 (2 m, 4H, CH$_2$CH$_2$), 2.45 (t, 2H, CH$_2$C=O ester), 3.87 (s, 3H, OMe), 4.50 (s, 2H, CH$_2$C=O ketone), 7.07 and 8.05 (2d, 4H, Ar—H), 7.47, 8.23, 8.35 (3 m, 3H, Ar—H).

LC-MS: MN$^+$ 372.

Example 3

Synthesis of 2-n-butyl-3-(4-methoxybenzoyl)-5-nitrobenzofuran (compound of the formula Ia) using an unmodified molecular sieve (Merck; 0.5 nm pores; 2 mm beads)

50 ml of dry xylene, 2.10 ml (8.89 mmol) of tri-n-butylamine and 10 g of a commercially available, unmodified molecular sieve (Merck; 0.5 nm pores; 2 mm beads) were heated under reflux using a Dean-Stark condenser. 2.20 g (5.92 mmol) of 2-(2-pentanoyloxy-5-nitrophenyl)-1-(4-methoxyphenyl)-ethanone (example 2) dissolved in 5 ml of dry xylene were added to the reaction mixture. After 8 h LC-MS analysis indicated the complete consumption of the 2-(2-pentanoyloxy-5-nitrophenyl)-1-(4-methoxyphenyl)-ethanone and the reaction mixture was cooled to room temperature. The molecular sieve was filtered off and the organic layer was washed once with 25 ml of 1N aqueous HCl, 10 ml of water and dried over MgSO$_4$. After evaporation of the solvent the product crystallized on standing to give 1.86 g (89%) of the title compound.

$^1$H NMR (DMSO-d$_6$): 0.82 (t, 3H, CH$_3$), 1.25 and 1.68 (2 m, 4H, CH$_2$CH$_2$), 2.85 (t, 2H, CH$_2$), 3.87 (s, 3H, OMe), 7.15 and 7.85 (2d, 4H, Ar—H), 7.95 (m, 1H, Ar—H), 8.25 (m, 2H, Ar—H). LC-MS: MN$^+$ 354

Example 4

Synthesis of 2-n-butyl-3-(4-methoxybenzoyl)-5-nitrobenzofuran (compound of the formula Ia) using an unmodified molecular sieve (Riedel-de-Haen; 0.4 nm pores; 2 mm beads)

50 ml of dry xylene, 2.10 ml (8.89 mmol) of tri-n-butylamine and 10 g of commercially available, unmodified molecular sieve (Riedel-de-Haen; 0.4 nm pores; 2 mm beads) were heated under reflux using a Dean-Stark condenser. 2.20 g (5.92 mmol) of 2-(2-pentanoyloxy-5-nitrophenyl)-1-(4-methoxyphenyl)-ethanone (example 2) dissolved in 5 ml of dry xylene were added to the reaction mixture. After 8 h LC-MS analysis indicated the complete consumption of the 2-(2-pentanoyloxy-5-nitrophenyl)-1-(4-methoxyphenyl)-ethanone and the reaction mixture was cooled to room temperature. The molecular sieve was filtered off and the organic layer was washed once with 25 ml of 1N aqueous HCl, 10 ml of water and dried over MgSO$_4$. After evaporation of the solvent the product crystallized on standing to give 1.80 g (86%) of the title compound.

Example 5

Synthesis of 2-n-butyl-3-(4-methoxybenzoyl)-5-nitrobenzofuran (compound of the formula Ia) using recovered molecular sieve 50 ml of dry xylene, 2.10 ml (8.89 mmol) of tri-n-butylamine and 10 g of the recovered molecular sieve from example 3 were heated under reflux using a Dean-Stark condenser. 2.20 g (5.92 mmol) of 2-(2-pentanoyloxy-5-nitrophenyl)-1-(4-methoxyphenyl)-ethanone (example 2) dissolved in 5 ml of dry xylene were added to the reaction mixture. After 8 h LC-MS analysis indicated the complete conversion of the 2-(2-pentanoyloxy-5-nitrophenyl)-1-(4-methoxyphenyl)-ethanone and the reaction mixture was cooled to room temperature. The molecular sieve was filtered off and the organic layer was washed once with 25 ml of 1N aqueous HCl, 10 ml of water and dried over MgSO$_4$. After evaporation of the solvent the product crystallized on standing to give 1.62 g (77%) of the title compound.

Example 7

Synthesis of 2-n-butyl-3-(4-hydroxybenzoyl)-5-nitrobenzofuran (compound of the formula Ib) at 200° C.

1.85 g (5.25 mmol) of 2-n-butyl-3-(4-methoxybenzoyl)-5-nitrobenzofuran (from example 3) were dissolved in 5.84 g (26.32 mmol) of tri-n-butylamine hydrochloride at 200° C. After 4 h LC-MS indicated the complete consumption of the starting material and the reaction mixture was cooled to room temperature. After addition of 20 ml of water and 50 ml MTBE the phases were separated, the organic layer was washed once with 25 ml of 1M HCl and 20 ml of water, dried over MgSO$_4$ and evaporated. Flash chromatography gave the title compound which crystallized to yield 1.50 g (83%).

$^1$H NMR (DMSO-d$_6$): 0.82 (t, 3H, CH$_3$), 1.25 and 1.68 (2 m, 4H, CH$_2$CH$_2$), 2.85 (t, 2H, CH$_2$), 6.92 and 7.75 (2d, 4H, Ar—H), 7.95 (m, 1H, Ar—H), 8.25 (m, 2H, Ar—H), 10.65 (s, 1H, OH).

Example 8

Synthesis of 2-n-butyl-3-(4-hydroxybenzoyl)-5-nitrobenzofuran (compound of the formula Ib) at 150° C.

1.50 g (4.25 mmol) of 2-n-butyl-3-(4-methoxybenzoyl)-5-nitrobenzofuran (Ia) were dissolved in 4.71 g (21.2 mmol) of tri-n-butylamine-hydrochloride at 150° C. After 16 h LC-MS analysis indicated the complete consumption of the starting material and the reaction mixture was cooled to room temperature. After addition of 20 ml of water and 50 ml MTBE the phases were separated, the organic layer was washed once with 25 ml of 1M HCl and 20 ml of water, dried over MgSO$_4$ and evaporated. Flash chromatography gave the title compound which crystallized to yield 1.10 g (76%).

Example 9

One-pot synthesis of 2-n-butyl-3-(4-hydroxybenzoyl)-5-nitrobenzofuran (compound of the formula Ib)

50 ml of dry xylene, 2.1 ml (8.9 mmol) of tri-n-butylamine and 10 g of the recovered molecular sieve from example 3 were heated under reflux using a Dean-Stark condenser. Then 2.20 g (5.92 mmol) of 2-(2-pentanoyloxy-5-nitrophenyl)-1-(4-methoxyphenyl)-ethanone (example 2) dissolved in 5 ml of dry xylene were added to the reaction mixture. After 8 h LC-MS analysis indicated the complete consumption of the starting material. The reaction mixture was cooled to room temperature and the molecular sievel was filtered off. After evaporation of the solvent, 2.1 ml (8.9 mmol) of tri-n-butylamine were added followed by the addition of 17.8 mmol of gaseous HCl. The resulting mixture was heated at 200° C. for 4 h until LC-MS analysis indicated the complete consumption of the 2-n-butyl-3-(4-methoxybenzoyl)-5-nitrobenzofuran. The reaction mixture was cooled to room temperature and 20 ml of water and 50 ml MTBE were added. The organic phase was washed once with 25 ml of 1M aqueous HCl and 20 ml of water dried over MgSO$_4$ and concentrated to dryness. Flash chromatography of the residue provided the pure title compound which crystallized directly to yield 1.30 g (65%).

Example 10

Synthesis of 2-n-butyl-3-(4-methoxybenzoyl)-5-nitrobenzofuran (compound of the formula Ia) using Fe-BEA type zeolite 15 ml of dry toluene, 2.10 ml (8.89 mmol) of tri-n-butylamine and 1 g of a commercially available synthetic zeolite composed of ca. 10% Al$_2$O$_3$, ca. 80% SiO$_2$ and ca. 10% Fe$_2$O$_3$ (Fe-BEA type, powder) were heated under reflux using a Dean-Stark condenser and 2.20 g (5.92 mmol) of 2-(2-pentanoyloxy-5-nitrophenyl)-1-(4-methoxyphenyl)-ethanone (example 2) dissolved in 5 ml of dry toluene were added to the reaction mixture. After 24 hours LC-MS analysis indicated a ca. 95% conversion of the 2-(2-pentanoyloxy-5-nitrophenyl)-1-(4-methoxyphenyl)-ethanone and the reaction mixture was cooled to room temperature. The zeolite was filtered off and the organic layer was washed once with 25 ml of 1N aqueous HCl, 10 ml of water and dried over $MgSO_4$. After evaporation of the solvent the product crystallized on standing to give 1.60 g (76%) of the title compound.

Example 11

Synthesis of 2-n-butyl-3-(4-methoxybenzoyl)-5-nitrobenzofuran (a compound of the formula Ia) using an iron-doped montmorillonite catalyst The iron-doped montmorillonite catalyst was prepared as described in Helv. Chim. Acta, vol. 70, 577-586 (1987). Dry toluene (15 ml) 2.10 ml (8.89 mmol) of tri-n-butylamine and 0.5 g of the iron-doped montmorillonite catalyst were heated under reflux using a Dean-Stark condenser and 2.20 g (5.92 mmol) of 2-(2-pentanoyloxy-5-nitrophenyl)-1-(4-methoxyphenyl)-ethanone (example 2) dissolved in 5 ml of dry toluene were added. After 2.5 hours LC-MS analysis showed a 100% conversion of the 2-(2-pentanoyloxy-5-nitrophenyl)-1-(4-methoxyphenyl)-ethanone and the reaction mixture was cooled to room temperature. The catalyst was filtered off and the organic layer was washed once with 20 ml of 1N aqueous HCl, 20 ml of water and dried over $MgSO_4$. Yield of the title compound: 1.92 g (92%)

Example 12

Synthesis of 2-n-butyl-3-(4-methoxybenzoyl)-5-nitrobenzofuran (a compound of the formula Ia) using iron-, zinc- or titanium-doped molecular sieves a) Preparation of the Iron-, Zinc- and Titanium-Doped Molecular Sieves

Commercially available molecular sieves from Merck (Darmstadt, Germany; 0.5 nm pores; 2 mm beads) were doped with iron, zinc or titanium. Three samples each of 5 g of the unmodified molecular sieve were stirred for 12 hours at room temperature with 0.40 g of $FeCl_3$, 0.27 g of $ZnCl_2$ or 0.19 g of $TiCl_4$, respectively, in 30 ml of dry dichloromethane. Subsequently each batch was filtered, thoroughly washed with 50 ml dry dichloromethane and dried in vacuum.

b) Synthesis of 2-n-butyl-3-(4-methoxybenzoyl)-5-nitrobenzofuran

Each of three flasks containing 0.37 g (1.00 mmol) of 2-(2-pentanoyloxy-5-nitrophenyl)-1-(4-methoxyphenyl)-ethanone (example 2) and 0.37 g (2.00 mmol) of tri-n-butylamine in 3 ml of refluxing toluene was charged with ca. 100 mg of the iron-, zinc- or titanium-doped molecular sieves and the reactions were monitored by LC-MS. After 30 min almost complete conversion into the target compound was achieved in both batches containing the iron- and zinc-doped molecular sieves (Fe 98% and Zn 90% percent integrated product peak area at 254 nanometer relative to unconsumed starting material) whereas the titanium-doped molecular showed a slower conversion up to 70% (percent integrated product peak area at 254 nanometer relative to unconsumed starting material).

Example 13

Synthesis of 2-n-butyl-3-(4-methoxybenzoyl)-5-nitrobenzofuran (compound of the formula Ib) using 1-butyl-4-methylpyridinium tetrafluoroborate as ionic solvent and dry Hydrochloric gas as reagent 30 g (84.9 mmol) of (2-Butyl-5-nitrobenzofuran-3-yl)(4-methoxyphenyl)methanone (compound of the formula Ia, HPLC-Rt: 19.3 min) was heated in 150 g (632.5 mmol) 1-butyl-4-methylpyridinium tetrafluoroborate to 150-155° C. The resulting solution was fumigated with dry gaseous HCl. After 20 h an HPLC-analysis indicated the end of the reaction (<1% of starting material). The fumigating was stopped and the reaction mixture was cooled to 80-85° C. Remaining starting material was extracted with 4×120 ml toluene at 80-85° C. The product containing phase was distilled under vacuum to eliminate last traces of toluene. At 50-60° C. 250 ml of water was added and the resulting solution was cooled to 20° C. within 1 h. The crystallisation started at 40-45° C. After stirring for 1 h at 20-25° C. the suspension was cooled down to 5° C. The product was filtered of, washed with 100 ml of water and suspended in 75 g of acetic acid. After heating to 70° C. 32 g of water was added dropwise to the solution. The mixture was cooled to 5° C. within 2 h. The resulting suspension was stirred for further 2 h at 5° C., filtered and washed with 50 ml acetic acid/water 1:1 (v/v) to give 21.5 g (74.6%) with an LC purity of 99.5%.

HPLC-Rt: 17.5 min

| HPLC conditions: | Column: | HALO ™-RP-Amide |
| --- | --- | --- |
| | Flow: | 0.8 ml/min |
| | Detection: | UV (275 nm) |
| | Solvent A: | 0.77 g $NH_4OC(O)CH_3$ + 900 ml water + 100 ml acetonitrile |
| | Solvent B. | 100% acetonitrile |
| | Gradient: | min     % B |
| | | 0     20 |
| | | 0.1     20 |
| | | 8     40 |
| | | 20     55 |
| | | 21     90 |
| | | 24     90 |
| | | 24.1     20 |
| | | 30     20 |

In a similar manner to example 13 the reaction was carried out in 1-butyl-pyridinium chloride, 3-butyl-1-methyl-3H-imidazolium chloride and 3-ethyl-1-methyl-3H-imidazolium chloride instead of 1-butyl-4-methylpyridinium tetrafluoroborate.

| Example | Amount of compound of formula Ia | Ionic liquid (amount of ionic liquid) | Reaction time and temperature | HPLC-area-%* of compound of formula Ib in the reaction mixture, without work-up |
| --- | --- | --- | --- | --- |
| 14 | 5 g | 1-butyl-pyridinium chloride (20 g) | 8 h 130-135° C. | 96.4 |

-continued

| Example | Amount of compound of formula Ia | Ionic liquid (amount of ionic liquid) | Reaction time and temperature | HPLC-area-%* of compound of formula Ib in the reaction mixture, without work-up |
|---|---|---|---|---|
| 15 | 5 g | 3-ethyl-1-methyl-3H-imidazolium chloride (20 g) | 13 h 130-135° C. | 95.4 |
| 16 | 5 g | 3-butyl-1-methyl-3H-imidazolium chloride (20 g) | 12 h 130-135° C. | 94.8 |

*HPLC-area-% gives the percentage of the respective area under the HPLC graph.

The invention claimed is:

1. A process for preparing a compound of the formula Ia

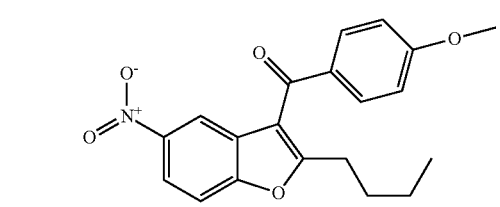

or a salt thereof;
which comprises

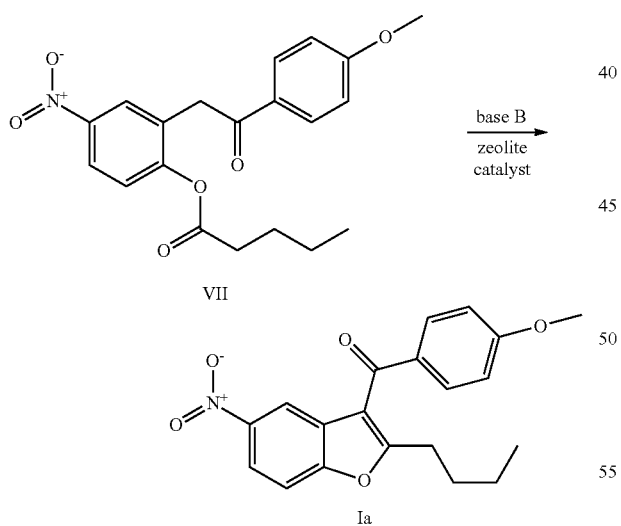

heating a compound of the formula VII with a base B and a zeolite catalyst, wherein base B is selected from the group consisting of diisopropylethylamine, tri-n-butylamine, tri-n-propylamine, N,N-dimethyaniline, N,N-diethylaniline, N-methyl-imidazole, N-ethyl-imidazole, N-propyl-imidazole, N-butyl-imidazole, collidine, 2,6-lutidine, 1,4-diazabicyclo-[2,2,2]-octane, 2,2,6,6-tetramethyl-piperidine and quinuclidine.

2. A process as claimed in claim 1 for preparing a compound of the formula Ib

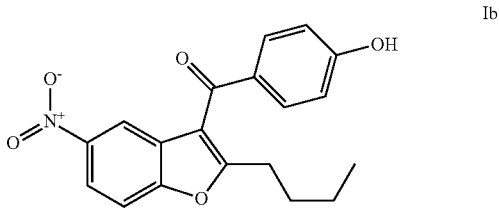 [SMILES: CCCCc1oc2ccc([N+](=O)[O-])cc2c1C(=O)c1ccc(O)cc1]

or a salt thereof;
which comprises

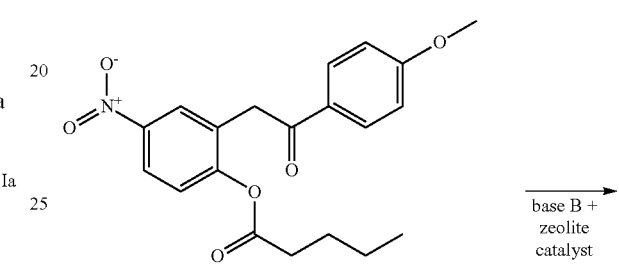

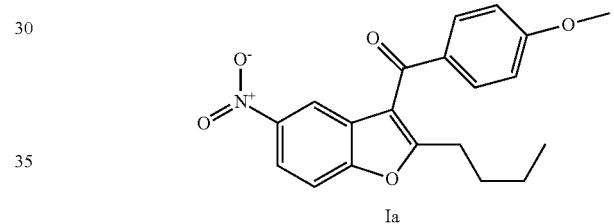

a) heating the ester of the formula VII with a base B and a zeolite catalyst providing the benzofuran of the formula Ia;
b) heating of the benzofuran of the formula Ia with HCl or HBr in the presence of a base B or alternatively heating of the benzofuran of formula Ia with HCl or HBr in an ionic liquid C providing the compound of the formula Ib, wherein base B is selected from the group consisting of diisopropylethylamine, tri-n-butylamine, tri-n-propylamine, N,N-dimethyaniline, N,N-diethylaniline, N-methyl-imidazole, N-ethyl-imidazole, N-propyl-imidazole, N-butyl-imidazole, collidine, 2,6-lutidine, 1,4- diazabicyclo-[2,2,2]-octane, 2,2,6,6-tetramethyl-piperidine and quinuclidine, and
wherein ionic liquid C is selected from the compounds of formula VIII and IX

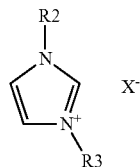

-continued

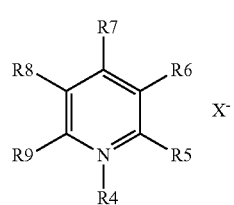

wherein
R2, R3 and R4 are independently of each other alkyl having 1, 2, 3, 4, 5, 6 or 7 carbon atoms;
R5, R6, R7, R8 and R9 are independently of each other H or alkyl having 1, 2, 3, 4, 5, 6 or 7 carbon atoms; and
X is F, Cl, Br, I, tetrafluoroborate, hexafluorophosphate, trifluoromethanesulfonate or hexafluoroantimonate.

3. The process as claimed in claim 1 or 2 for preparing a compound of the formula I

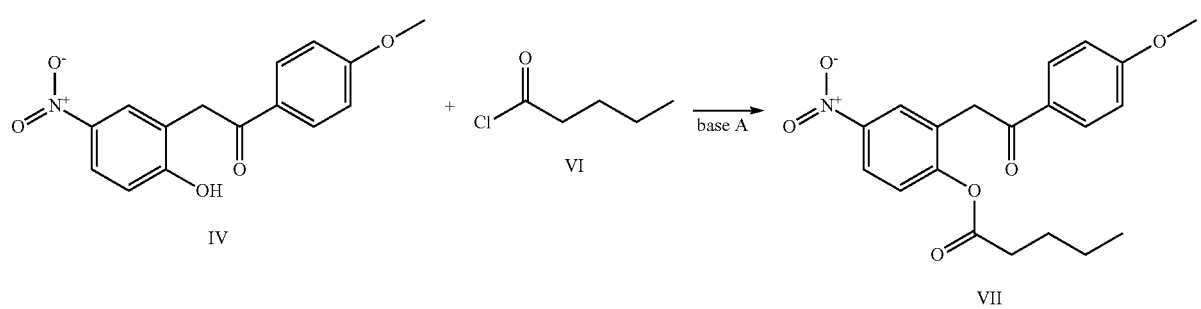

wherein
R1 is methoxy or hydroxyl;
or a salt thereof;
which comprises

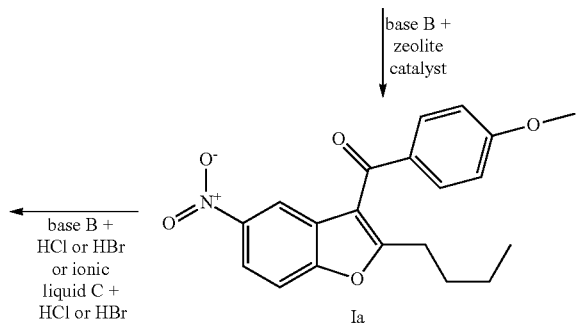

a) acylating the 2-(2-hydroxy-5-nitrophenyl)-1-(4-methoxyphenyl)-ethanone of the formula IV by the acid chloride of formula VI in the presence of a base A providing the new ester of the formula VII;
b) heating the ester of the formula VII with a base B and a zeolite catalyst providing the benzofuran of the formula Ia;
c) optionally heating the benzofuran of formula Ia with HCl or HBr in the presence of a base B or alternatively heating the benzofuran of formula Ia with HCl or HBr in an ionic liquid C providing the compound of the formula Ib,
wherein base B is selected from the group consisting of diisopropylethylamine, tri-n-butylamine, tri-n-propylamine, N,N-dimethyaniline, N-diethylaniline, N-methyl-imidazole, N-ethyl-imidazole, N-propyl-imidazole, N-butyl-imidazole, collidine, 2,6-lutidine, 1,4-diazabicyclo-[2,2,2]-octane, 2,2,6,6-tetramethylpiperidine and quinuclidine, and wherein ionic liquid C is selected from the compounds of formula VIII and IX

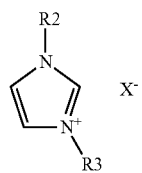

VIII

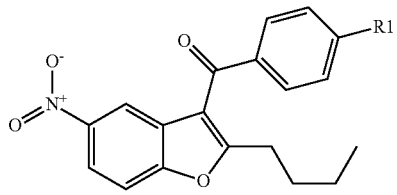

I wherein
R1 is methoxy or hydroxyl;
or a salt thereof;
which comprises,

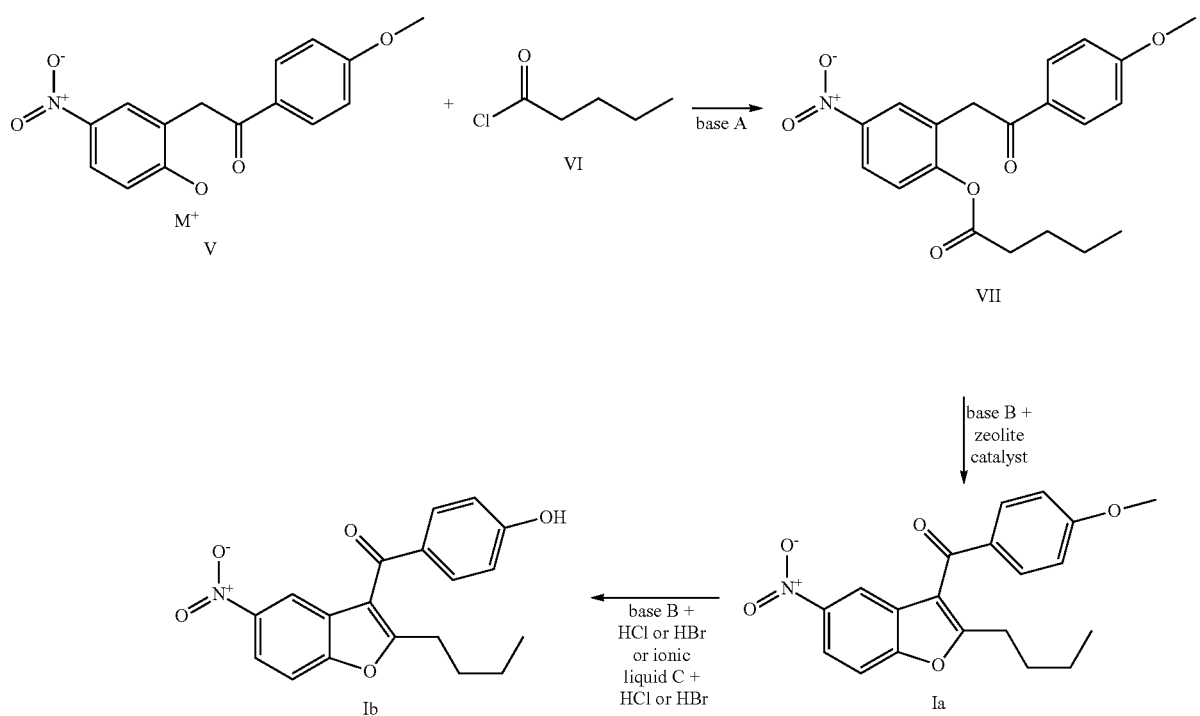

-continued

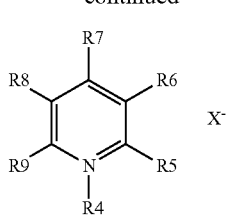

IX wherein
R2, R3 and R4 are independently of each other alkyl having 1, 2, 3, 4, 5, 6 or 7 carbon atoms;
R5, R6, R7, R8 and R9 are independently of each other H or alkyl having 1, 2, 3, 4, 5, 6 or 7 carbon atoms; and
X is F, Cl, Br, I, tetrafluoroborate, hexafluorophosphate, trifluoromethanesulfonate or hexafluoroantimonate.

4. The process as claimed in claim 1 or 2 for preparing a compound of the formula I, a) reacting a compound of the formula V, wherein M is Na or K, with an acid chloride of the formula VI in the presence of a base A providing the ester of the formula VII;
b) heating the ester of the formula VII with a base B and a zeolite catalyst providing the benzofuran of the formula Ia;
c) optionally heating the benzofuran of formula Ia with HCl or HBr in the presence of a base B or alternatively heating of the benzofuran of formula Ia with HCl or HBr in an ionic liquid C providing the compound of the formula Ib, wherein base B is selected from the group consisting of diisopropylethylamine, tri-n-butylamine, tri-n-propylamine, N,N-dimethyaniline, N,N-diethylaniline, N-methyl-imidazole, N-ethyl-imidazole, N-propyl-imidazole, N-butyl-imidazole, collidine, 2,6-lutidine, 1,4-diazabicyclo-[2,2,2]-octane, 2,2,6,6-tetramethyl-piperidine and quinuclidine, and wherein ionic liquid C is selected from the compounds of formula VIII and IX

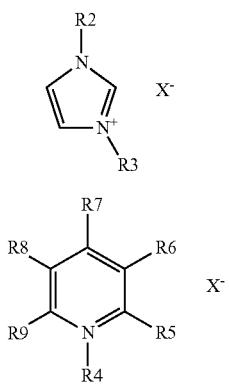

wherein

R2, R3 and R4 are independently of each other alkyl having 1, 2, 3, 4, 5, 6, or 7 carbon atoms;

R5, R6, R7, R8 and R9 are independently of each other H or alkyl having 1, 2, 3, 4, 5, 6 or 7 carbon atoms; and X is F, Cl, Br, I, tetrafluoroborate, hexafluorophosphate, trifluoromethanesulfonate or hexafluoroantimonate.

5. The process claimed in claim 2 wherein the conformation of the benzofuran of the formula Ia to the compound of the formula Ib is carried out by heating of the benzofuran of formula Ia with HCl or HBr in the presence of the base B.

6. The process claimed in claim 2 wherein the conformation of the benzofuran of the formula Ia to the compound of the formula Ib is carried out by heating of the benzofuran of formula Ia with HCl or HBr in the ionic liquid C.

7. The process claimed in claim 1 wherein the zeolite catalyst is a natural or synthetic alumosilicate.

8. The process claimed in claim 1 wherein the zeolite catalyst is a modified alumosilicate containing variable amounts of at least one metal ion selected from the group of iron, manganese, titanium, zirconium, zink or scandium.

9. The process as claimed in claim 2 wherein the base B used in the reaction of the compound of the formula Ia to the compound of the formula Ib is the same as the base B used in the reaction of the compound of the formula VII to the compound of the formula Ia.

10. The process as claimed in claim 2 wherein the compound of the formula Ia is isolated and then is reacted as claimed to the compound of the formula Ib as claimed in claim 2.

11. The process as claimed in claim 2 wherein the compound of the formula Ia is prepared in situ without being isolated and then is reacted to the compound of the formula Ib as claimed in claim 2.

12. The process of claim 2 wherein ionic liquid C is ionic liquid C is selected from the group consisting of 1-butyl-4-methylpyridinium tetrafluoroborate, 1-butyl-pyridinium chloride, 3-butyl-1-methyl-3H-imidazolium chloride, 3-ethyl-1-methyl-3H-imidazolium chloride, 1-butyl-2-methylpyridinium tetrafluoroborate, 1-butyl-3-methylpyridinium tetrafluoroborate, 1-butyl-pyridinium tetrafluoroborate, 3-butyl-1-methyl-3H-imidazolium tetrafluoroborate, and 3-ethyl-1-methyl-3H-imidazolium tetrafluoroborate.

\* \* \* \* \*